(12) United States Patent
Takei et al.

(10) Patent No.: US 8,545,225 B2
(45) Date of Patent: Oct. 1, 2013

(54) REDOX-CURING TYPE COMPOSITION

(75) Inventors: Mitsuru Takei, Kurashiki (JP); Mariko Sugiura, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 236 days.

(21) Appl. No.: 13/256,729

(22) PCT Filed: Mar. 1, 2010

(86) PCT No.: PCT/JP2010/053264
§ 371 (c)(1),
(2), (4) Date: Sep. 15, 2011

(87) PCT Pub. No.: WO2010/106903
PCT Pub. Date: Sep. 23, 2010

(65) Prior Publication Data
US 2012/0016094 A1    Jan. 19, 2012

(30) Foreign Application Priority Data
Mar. 18, 2009  (JP) ................................. 2009-066081

(51) Int. Cl.
C08F 4/40 (2006.01)
C08F 4/34 (2006.01)
C01B 13/36 (2006.01)
C01B 15/043 (2006.01)
C01D 5/00 (2006.01)
C01D 1/02 (2006.01)
A61K 6/083 (2006.01)

(52) U.S. Cl.
USPC ................ 433/228.1; 106/35; 260/998.11; 423/583; 423/636; 423/641; 433/226; 526/217; 526/229

(58) Field of Classification Search
USPC .............. 106/35; 260/998.11; 423/583, 636, 423/641; 433/226, 228.1; 526/217, 229
See application file for complete search history.

(56) References Cited

U.S. PATENT DOCUMENTS

| | | | |
|---|---|---|---|
| 4,259,117 A | 3/1981 | Yamauchi et al. | |
| 4,539,382 A | 9/1985 | Omura et al. | |
| 4,547,531 A | 10/1985 | Waknine | |
| 4,719,297 A | 1/1988 | Henne et al. | |
| 5,154,762 A * | 10/1992 | Mitra et al. | 106/35 |
| 6,491,807 B2 * | 12/2002 | Kimizuka et al. | 205/349 |
| 6,818,682 B2 | 11/2004 | Falsafi et al. | |
| 2008/0015279 A1 * | 1/2008 | Tokui et al. | 522/182 |
| 2008/0081889 A1 * | 4/2008 | Kawashima et al. | 526/181 |
| 2009/0299006 A1 | 12/2009 | Shinno et al. | |
| 2010/0087613 A1 | 4/2010 | Takei et al. | |

FOREIGN PATENT DOCUMENTS

| | | |
|---|---|---|
| JP | 52 113089 | 9/1977 |
| JP | 53 067740 | 6/1978 |
| JP | 53 069494 | 6/1978 |
| JP | 53 144939 | 12/1978 |
| JP | 58 128393 | 7/1983 |
| JP | 58 192891 | 11/1983 |
| JP | 3 057916 | 9/1991 |
| JP | 6 2651 | 1/1994 |
| JP | 2008 019183 | 1/2008 |
| WO | 02 085313 | 10/2002 |
| WO | 2006 016545 | 2/2006 |
| WO | 2007 135742 | 11/2007 |
| WO | 2008 090784 | 7/2008 |

OTHER PUBLICATIONS

International Search Report issued Jun. 8, 2010 in PCT/JP10/053264 filed Mar. 1, 2010.

* cited by examiner

*Primary Examiner* — Richard A Huhn

(74) *Attorney, Agent, or Firm* — Oblon, Spivak, McClelland, Maier & Neustadt, L.L.P.

(57) ABSTRACT

The present invention provides a redox-curing type composition that penetrates into a wet body, particularly into a tooth structure (dentin), is cured in an accelerated manner by the moisture contained in the wet body, thereby exhibits a higher bond strength than those of conventional redox-curing type compositions, and has satisfactory storage stability. The present invention is a redox-curing type composition including a polymerizable monomer (a) having an acidic group, a polymerizable monomer (b) having no acidic group, a powdery inorganic peroxide (c) with an average particle diameter of 0.01 to 50 μm, an amine-based reducing agent (d), and a polymerization accelerator (e). The amine-based reducing agent (d) includes an aromatic amine (d–1) and an aliphatic amine (d–2), and a weight ratio (d–1):(d–2) therebetween is 5:1 to 1:50.

7 Claims, No Drawings

REDOX-CURING TYPE COMPOSITION

TECHNICAL FIELD

The present invention relates to a redox-curing type composition, particularly to a redox-curing type composition that undergoes an accelerated curing reaction by being in contact with a wet body containing moisture.

BACKGROUND ART

Adhesive materials have been used for the restoration of wet bodies such as biological hard tissues like teeth and bones. As the adhesive materials for the wet bodies, resin-based curable compositions including a radical polymerizable monomer and a polymerization initiator have been widely used.

It is discussed to have the resin-based curable compositions include a radical polymerizable monomer having an acidic group and a polymerization initiator that cures highly efficiently the curable compositions containing the radical polymerizable monomer, in order to enhance the adhesive properties of the curable compositions to a wet body, particularly to biological hard tissues.

To bond a resin-based curable composition to a wet body, particularly to a tooth structure, it is necessary to allow the curable composition to penetrate into the tooth structure. A polymerizable monomer having a hydrophilic group and a polymerizable monomer having an acidic group in the curable composition penetrate into the tooth structure. When these components penetrate into the tooth structure, a curing reaction proceeds also inside the tooth structure near the interface between the tooth structure and the curable composition, forming a complex body of the curable composition and the tooth structure, that is, a resin-impregnated layer, thereby exhibiting a high bond strength.

The present applicants have proposed redox-curing type compositions each including: a radical polymerizable monomer; and an oxidizing agent and a reducing agent forming a redox polymerization initiator. As the reducing agent, a water-soluble reducing agent is dispersed in a powdery state in each redox-curing type composition so that the curing reaction of the composition is accelerated at an adhesion interface by the moisture in a wet body. For example, Patent Literature 1 proposes a redox curing-type nonaqueous curable composition including a liquid radical polymerizable monomer, an organic peroxide, and a powdery water-soluble reducing compound. The powdery water-soluble reducing compound is dispersed in the liquid radical polymerizable monomer. Patent Literature 2 proposes a multi-part redox-curing type composition including: a first part in which at least an oxidizing agent is dissolved in a first radical polymerizable monomer containing a radical polymerizable monomer having an acidic group and/or a hydrophilic group; and a second part in which at least an aromatic sulfinate is dispersed in a second radical polymerizable monomer containing a radical polymerizable monomer having neither an acidic group nor a hydrophilic group. These redox-curing type compositions achieved higher bond strengths to tooth structure, particularly dentin than those of conventional ones.

However, in Patent Literature 1, since a water-insoluble organic peroxide is used as the oxidizing agent of the redox polymerization initiator, it fails to penetrate sufficiently into a tooth structure, particularly into dentin, and fails to contribute sufficiently to the curing reaction inside the tooth structure. Thus, the bond strength is left to be improved.

Also in Patent Literature 2, since the oxidizing agent studied is a water-insoluble organic peroxide, it fails to penetrate sufficiently into a tooth structure, particularly into dentin, and fails to contribute sufficiently to the curing reaction inside the tooth structure. Thus, the bond strength is left to be improved.

In contrast, Patent Literature 3 discloses a dental cement including: a first paste containing a specified (meth)acrylate monomer, a filler, and an amine compound; and a second paste containing a specified (meth)acrylate monomer, a filler, an organic aromatic compound containing at least one —$SO_2$— group as a polymerization catalyst, and a peroxide. More specifically, in this dental cement, the second paste contains a water-soluble inorganic peroxide serving as an oxidizing agent and the first paste contains water so that the inorganic peroxide is dissolved and accelerates the curing reaction when these pastes are mixed with each other. However, the bond strength of the dental cement is in a range equivalent to the ranges of the bond strengths of conventional dental cements. Moreover, there is a problem in that the water contained in the paste lowers the storage stability of the paste, and furthermore, the volatilization of the water during storage changes the composition of the paste, leading to possible variations in the curing time and curing property. An attempt to suppress the water evaporation requires complicated storage conditions, which is another problem. Moreover, when the composition contains water, a hydrophilic component and a hydrophobic component are separated from each other after the cement is prepared by mixing, and a cured product of the cement is degraded because the hydrophilic component absorbs water or is dissolved when immersed in water for a long period of time. This causes problems such as decreases in the bond durability, strength and transparency, and a change in color tone.

CITATION LIST

Patent Literature

PTL 1: WO 2006/016545
PTL 2: WO 2008/090784
PTL 3: JP 2008-19183 A

SUMMARY OF INVENTION

Technical Problem

The present invention is intended to provide a redox-curing type composition that penetrates into a wet body, particularly into a tooth structure (dentin), is cured in an accelerated manner by the moisture contained in the wet body, thereby exhibits a higher bond strength than those of conventional redox-curing type compositions, and has satisfactory storage stability.

Solution to Problem

The present invention that has accomplished the above-mentioned object is a redox-curing type composition including a polymerizable monomer (a) having an acidic group, a polymerizable monomer (b) having no acidic group, a powdery inorganic peroxide (c) with an average particle diameter of 0.01 to 50 μm, an amine-based reducing agent (d), and a polymerization accelerator (e). The amine-based reducing agent (d) includes an aromatic amine (d-1) and an aliphatic amine (d-2), and a weight ratio (d-1):(d-2) therebetween is 5:1 to 1:50.

Preferably, the redox-curing type composition of the present invention is substantially free from water.

Preferably, the polymerization accelerator (e) is at least one selected from the group consisting of sodium benzenesulfinate, sodium p-toluenesulfinate, sodium 2,4,6-triisopropylbenzenesulfinate, sodium sulfite, potassium sulfite, calcium sulfite, ammonium sulfite, sodium bisulfate, and potassium bisulfate. Preferably, at least a part of the polymerization accelerator (e) is contained in a powdery state.

Preferably, the inorganic peroxide (c) is peroxodisulfate. Preferably, the inorganic peroxide (c) is obtained by a freeze dry method.

Also, the present invention is a dental cement including:

a first part containing a powdery inorganic peroxide (c) with an average particle diameter of 0.01 to 50 μm; and a second part containing an amine-based reducing agent (d). The amine-based reducing agent (d) includes an aromatic amine (d–1) and an aliphatic amine (d–2), and a weight ratio (d–1):(d–2) therebetween is 5:1 to 1:50.

A polymerizable monomer (a) having an acidic group, a polymerizable monomer (b) having no acidic group, and a polymerization accelerator (e) each are contained in one or both of the first part and the second part.

Advantageous Effects of Invention

The present invention provides a redox-curing type composition that exhibits a higher bond strength to a wet body, particularly to a tooth structure (dentin) than those of conventional redox-curing type compositions, and has satisfactory storage stability.

DESCRIPTION OF EMBODIMENTS

As a result of intensive studies to solve the above-mentioned problems, the present inventors have found it possible to allow the redox-curing type composition to exhibit a higher bond strength by using an inorganic peroxide together with an amine-based reducing agent including an aliphatic amine and an aromatic amine that are in a specified combination at a specified ratio, and by dispersing the powdery inorganic peroxide with a specified average particle diameter in the redox-curing type composition, even when the composition is free from water. Thus, the present invention has been completed.

Presumably, the reason is as follows. In a case where the redox-curing type composition contains an inorganic peroxide as an oxidizing agent, water must be added into the composition to dissolve the inorganic peroxide at the time of reaction unless the inorganic peroxide has a very small diameter. If water is not added into the composition, the large particle diameter lowers the reaction efficiency, requiring a longer curing time. In order to set the curing time in an appropriate range, it is necessary to add a large amount of a reducing agent (amine). In this case, there is a problem in that the color tone stability of the cured product is low. Moreover, no addition of water lowers the bond strength of the composition to an adherend. For these reasons, water needs to be added unless the inorganic peroxide has a very small diameter. However, when the composition contains water, the storage stabilities of the polymerizable monomer, etc. in the composition are lowered, and furthermore, the volatilization of the water during storage changes the composition of the redox-curing type composition, leading to possible variations in the curing time and curing property. Moreover, when the composition contains water, a hydrophilic component and a hydrophobic component are separated from each other after the composition is prepared (after the cement is prepared by mixing), and a cured product of the cement is degraded because the hydrophilic component absorbs water or is dissolved when immersed in water for a long period of time. This causes problems such as a change in color tone, and decrease in transparency.

In contrast, in the composition of the present invention, the curing reaction can proceed highly efficiently even when the composition is free from water because the inorganic peroxide is used together with the amine-based reducing agent prepared in a specified combination at a specified ratio, and the inorganic peroxide is formed of fine powder particles with a specified average particle diameter (an average particle diameter of 0.01 to 50 μm). More specifically, the composition of the present invention cures in a short curing time, and thereby does not require the reducing agent in a large amount that affects the color tone. Moreover, the fine powdery inorganic peroxide present at the adhesion interface is dissolved in the moisture present on the surface of a wet body. In the portion in which the fine powdery inorganic peroxide is dissolved in the moisture, the concentration of the inorganic peroxide is high, and the inorganic peroxide and the amine-based reducing agent encounter highly frequently each other in a molecular state. In other words, a redox reaction, that is, a radical formation reaction, proceeds easily. The portion in which the fine powdery inorganic peroxide is dissolved in the moisture is at the adhesion interface and inside a resin-impregnated layer formed on the wet body, which are important for adhesive property. On the other hand, since the inorganic peroxide in the composition of the present invention is present in a powdery (solid) state without being dissolved in the polymerizable monomer, it is possible to control appropriately the frequency at which the inorganic peroxide and the amine-based reducing agent dissolved in the polymerizable monomer encounter each other in a molecular state according to the particle diameter and concentration of the inorganic peroxide. Thus, a necessary working time can be secured. As a result, it is possible to enhance selectively the polymerization curabilities at the adhesion interface and inside the resin-impregnated layer that need to be enhanced. Furthermore, use of the amine-based reducing agent including an aromatic amine and an aliphatic amine combined at a specified ratio allows the amine-based reducing agent to have an increased redox reactivity with the inorganic peroxide, and makes it possible to enhance the polymerization curing property. This is the reason why the composition of the present invention exhibits a high bond strength to a wet body.

The average particle diameter in the present invention is a mean volume diameter. The mean volume diameter can be determined by, for example, an image analysis on an electron microscope photograph of 100 particles or more, using an image analysis software (Mac-View produced by Mountech Co., Ltd., for example).

The polymerizable monomer (a) having an acidic group is a component that, by having an acidic group, exhibits strong chemical and physical interactions with a wet body, such as a tooth structure and a bone, and penetrates into the wet body to provide the composition with a high bond strength.

As the polymerizable monomer (a) having an acidic group, there can be mentioned a polymerizable monomer having at least one acidic group such as a phosphate group, a pyrophosphate group, a thiophosphate group, a phosphonate group, a carboxylic acid group and a sulfonate group, and at least one polymerizable group such as an acryloyl group, a methacryloyl group, a vinyl group and a styrene group. Specific examples of the polymerizable monomer (a) having an acidic group are as follows.

Examples of the polymerizable monomer having a phosphate group include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl 2-bromoethyl hydrogen phosphate, 2-methacryloyloxyethyl (4-methoxyphenyl) hydrogen phosphate and 2-methacryloyloxypropyl (4-methoxyphenyl) hydrogen phosphate, and polymerizable monomers having a phosphate group and acid chlorides, alkali metal salts and ammonium salts of them described in JP 52(1977)-113089 A, JP 53(1998)-67740 A, JP 53(1998)-69494 A, JP 53(1998)-144939 A, JP 58(1983)-128393 A and JP 58(1983)-192891 A.

Examples of the polymerizable monomer having a pyrophosphate group include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate and bis [10-(meth)acryloyloxydecyl] pyrophosphate, and acid chlorides, alkali metal salts and ammonium salts of them.

Examples of the polymerizable monomer having a thiophosphate group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate and 20-(meth)acryloyloxyicosyl dihydrogen thiophosphate, and acid chlorides, alkali metal salts and ammonium salts of them.

Examples of the polymerizable monomer having a phosphonate group include 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth)acryloyloxyhexyl-3-phosphonoacetate and 10-(meth)acryloyloxydecyl-3-phosphonoacetate, and acid chlorides, alkali metal salts and ammonium salts of them.

Examples of the polymerizable monomer having a carboxylic acid group include a polymerizable monomer having one carboxyl group in a molecule and a polymerizable monomer having a plurality of carboxyl groups in a molecule.

Examples of the polymerizable monomer having one carboxyl group in a molecule include (meth)acrylic acid, N-(meth)acryloyl glycine, N-(meth)acryloyl aspartic acid, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate and 2-(meth)acryloyloxyethyl hydrogen malate, and acid halides of them.

Examples of the polymerizable monomer having a plurality of carboxyl groups in a molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate and 2-(meth)acryloyloxyethyl-3'-(meth)acryloyloxy-2'-(3,4-dicarboxybenzoyloxy)propyl succinate, and anhydrides and acid halides of them.

Examples of the polymerizable monomer having a sulfonate group include 2-(meth)acrylamide-2-methylpropanesulfonic acid, styrenesulfonic acid, and 2-sulfoethyl (meth)acrylate.

The above-mentioned polymerizable monomers having an acidic group may be used independently or a plurality of them may be used in combination. Among these polymerizable monomers having an acidic group, 10-(meth)acryloyloxydecyl dihydrogen phosphate, 1,3-di(meth)acryloyloxypropyl dihydrogen phosphate, 2-(meth)acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropanesulfonic acid, and 11-(meth)acryloyloxyundecane-1,1-dicarboxylic acid are used preferably because a high bond strength is obtained when they are used in a redox-curing type composition for dental use.

The amount of the polymerizable monomer (a) having an acidic group to be added preferably is 1 to 50 parts by weight, more preferably 5 to 40 parts by weight, and further preferably 10 to 30 parts by weight, in 100 parts by weight of the total amount of the polymerizable monomer components included in the redox-curing type composition of the present invention. When the amount of the polymerizable monomer having an acidic group to be added is 1 part by weight or more, a satisfactory bond strength is obtained. When the amount of the polymerizable monomer having an acidic group to be added is 50 parts by weight or less, the redox-curing type composition has appropriate curing property and also maintains the bond strength satisfactorily.

The polymerizable monomer (b) having no acidic group is a polymerizable monomer that undergoes a radical polymerization reaction initiated with a redox polymerization initiator so as to be polymerized. The number of kinds of the polymerizable monomers included in the polymerizable monomer (b) having no acidic group in the present invention is not limited to one and may be two or more. As the polymerizable monomer (b) having no acidic group, the following water-soluble polymerizable monomer and hydrophobic polymerizable monomer can be mentioned.

The water-soluble polymerizable monomer is a monomer that has a water solubility of 10% by weight or more at 25° C.

Preferably, the solubility of the water-soluble polymerizable monomer is 30% by weight or more. More preferably, the water-soluble polymerizable monomer can be dissolved in water at an arbitrary ratio at 25° C. The water-soluble polymerizable monomer accelerates the penetration of the components of the redox-curing type composition into the tooth structure. Also, the water-soluble polymerizable monomer itself penetrates into the tooth structure and bonds to an organic component (collagen) in the tooth structure. Examples of the water-soluble polymerizable monomer include 2-hydroxyethyl(meth)acrylate, 3-hydroxypropyl(meth)acrylate, 2-hydroxypropyl(meth)acrylate, 1,3-dihydroxypropyl(meth)acrylate, 2,3-dihydroxypropyl(meth)acrylate, 2-trimethylammoniumethyl(meth)acrylchloride, and polyethylene glycol di(meth)acrylate (having nine or more oxyethylene groups).

As the hydrophobic polymerizable monomer, there can be mentioned a crosslinkable polymerizable monomer having a water solubility of less than 10% by weight at 25° C. Examples thereof include an aromatic compound-type bifunctional polymerizable monomer, an aliphatic compound-type bifunctional polymerizable monomer, and trifunctional or higher polymerizable monomers. The hydrophobic polymerizable monomer enhances the mechanical strength, handling property, etc. of the redox-curing type composition.

Examples of the aromatic compound-type bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxydiphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromeritate. Among these, 2,2-bis(4-(3-methacryloyloxy)-2-hydroxypropoxyphenyl)propane and 2,2-bis(4-methacryloyloxypolyethoxyphenyl)propane are preferable.

Examples of the aliphatic compound-type bifunctional polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylenebis(2-carbamoyloxyethyl) dimethacrylate (commonly known as "UDMA"), and 1,2-bis(3-methacryloyloxy-2-hydroxypropyloxy)ethane. Among these, glycerol dimethacrylate, triethylene glycol di(meth)acrylate, neopentyl glycol dimethacrylate, 2,2,4-trimethylhexamethylenebis(2-carbamoyloxyethyl) dimethacrylate, and 1,2-bis(3-methacryloyloxy-2-hydroxypropyloxy)ethane are preferable.

Examples of the trifunctional or higher polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

The above-mentioned polymerizable monomers (b) having no acidic group (the water-soluble polymerizable monomers and the hydrophobic polymerizable monomers) may be added independently or a plurality of them may be added in combination, respectively. The amount of the water-soluble polymerizable monomer to be added preferably is 1 to 50 parts by weight, more preferably 5 to 40 parts by weight, and most preferably 10 to 30 parts by weight, in 100 parts by weight of the total amount of the polymerizable monomer components included in the redox-curing type composition. The amount of the hydrophobic polymerizable monomer to be added preferably is 10 to 95 parts by weight, more preferably 30 to 90 parts by weight, and further preferably 50 to 80 parts by weight, in 100 parts by weight of the total amount of the polymerizable monomer components included in the redox-curing type composition.

The inorganic peroxide (c) is an oxidizing agent component of the redox polymerization initiator. Examples of the inorganic peroxide (c) include peroxodisulfate and peroxodiphosphate. Out of these, peroxodisulfate is preferable from the viewpoint of redox reactivity. Specific examples of the peroxodisulfate include sodium peroxodisulfate, potassium peroxodisulfate, aluminum peroxodisulfate, and ammonium peroxodisulfate.

The above-mentioned peroxodisulfates may be used independently or a plurality of them may be used in combination. Among the peroxodisulfates, sodium peroxodisulfate, potassium peroxodisulfate, and ammonium peroxodisulfate are preferable.

The inorganic peroxide (c) is dispersed in a powdery state in the polymerizable monomer (a) having an acidic group and/or the polymerizable monomer (b) having no acidic group. The powdery inorganic peroxide (c) has an average particle diameter of 50 μm or less, preferably 20 μm or less, because an excessively large particle diameter slows the curing reaction. On the other hand, the average particle diameter is 0.01 μm or more because an excessively small particle diameter increases excessively the specific surface area of the powder and reduces the amount of the powdery inorganic peroxide (c) that can be dispersed in the composition. That is, the average particle diameter of the inorganic peroxide (e) is 0.01 to 50 μm, preferably 0.01 to 20 μm.

The shape of the powdery inorganic peroxide (c) is not particularly limited and may be any of various shapes such as a spherical shape, a needle shape, a plate shape, and a crushed shape. The powdery inorganic peroxide (c) can be produced by any of known methods such as a grinding method, a freeze dry method, and a reprecipitation method. Among these methods of producing the powdery inorganic peroxide (c), the freeze dry method and the reprecipitating method are preferable, and the freeze dry method is more preferable, from the viewpoint of the average particle diameter of the resultant powder.

The amount of the powdery inorganic peroxide (c) to be added preferably is 0.01 to 10 parts by weight, with respect to 100 parts by weight of the total amount of the polymerizable monomer components included in the redox-curing type composition of the present invention. When the amount to be added is less than 0.01 part by weight, the mechanical strength of the cured product and the bond strength may be lowered. On the other hand, when the amount to be added exceeds 10 parts by weight, the bond strength may also be lowered.

In the present invention, the amine-based reducing agent (d) is a reducing agent component of the redox polymerization initiator, and includes an aromatic amine (d–1) and an aliphatic amine (d–2). Use of the aromatic amine (d–1) and the aliphatic amine (d–2) combined at a specified ratio can increase the redox reactivity of the amine-based reducing agent (d) with the inorganic peroxide and thereby enhances the polymerization curing property of the composition.

As the aromatic amine (d–1), known aromatic secondary amine, aromatic tertiary amine, etc. may be used. Examples of the aromatic secondary amine or aromatic tertiary amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. Among these, N,N-di(2-hydroxyethyl)-p-toluidine is preferable from the viewpoint of redox reactivity.

Examples of the aliphatic amine (d–2) include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine tri(meth)acrylate, triethanolamine, trimethylamine, triethylamine, and tributylamine. Among these, the tertiary aliphatic amines are preferable from the viewpoint of redox reactivity, and particularly N-methyldiethanolamine, triethanolamine, and 2-(dimethylamino)ethyl methacrylate are preferable.

The weight ratio (d–1):(d–2) of the aromatic amine (d–1) and the aliphatic amine (d–2) is 5:1 to 1:50, preferably 1:1 to 1:30, and further preferably 1:1 to 1:15. When the ratio of the aromatic amine (d–1) added is higher than a weight ratio (d–1):(d–2) of 5:1, there is a problem in that the degree of discoloration increases. On the other hand, when the ratio of the aliphatic amine (d–2) added is higher than a weight ratio (d–1):(d–2) of 1:50, the redox reactivity falls and the polymerization curing property is lowered, leading to a possible decrease in the bond strength.

The amount of the amine-based reducing agent (d) (the total amount of the aromatic amine and the aliphatic amine) to be added preferably is 0.01 to 15 parts by weight, more preferably 0.05 to 10 parts by weight, and most preferably 0.1 to 5 parts by weight, with respect to 100 parts by weight of the total amount of the polymerizable monomer components included in the redox-curing type composition of the present invention. When the amount to be added is less than 0.01 parts by weight, the bond strength of the resultant redox-curing type composition to a wet body, such as a tooth structure, may be lowered. On the other hand, when the amount to be added exceeds 15 parts by weight, the color tone stability of the resultant redox-curing type composition may be lowered.

As the polymerization accelerator (e), the following compounds can be used, for example. As an aromatic sulfinate, lithium salts, sodium salts, potassium salts, rubidium salts, cesium salts, magnesium salts, calcium salts, strontium salts, iron salts, copper salts, zinc salts, ammonium salts, tetramethyl ammonium salts and tetraethyl ammonium salts of benzene sulfinic acid, p-toluene sulfinic acid, o-toluene sulfinic acid, ethyl benzene sulfinic acid, decyl benzene sulfinic acid, dodecyl benzene sulfinic acid, 2,4,6-trimethyl benzene sulfinic acid, 2,4,6-triisopropyl benzene sulfinic acid, chlorobenzene sulfinic acid, naphthalene sulfinic acid or the like are exemplified. As sulfite, sodium sulfite, potassium sulfite, calcium sulfite, and ammonium sulfite are exemplified. As bisulfite, sodium bisulfate and potassium bisulfate are exemplified. Among these, at least one selected from the group consisting of sodium benzenesulfinate, sodium p-toluenesulfinate, sodium 2,4,6-triisopropylbenzenesulfinate, sodium sulfite, potassium sulfite, calcium sulfite, ammonium sulfite, sodium bisulfate, and potassium bisulfate is used preferably.

These polymerization accelerator (e) may be used independently or a plurality of them may be used in combination. The amount of the polymerization accelerator (e) to be added preferably is 0.1 to 20 parts by weight, more preferably 0.2 to 15 parts by weight, and most preferably 0.5 to 10 parts by weight, with respect to 100 parts by weight of the total amount of the polymerizable monomer components included in the redox-curing type composition of the present invention. When the amount to be added is less than 0.1 parts by weight, the bond strength of the resultant redox-curing type composition to a wet body, such as a tooth structure, may be lowered. On the other hand, when the amount to be added exceeds 20 parts by weight, the mechanical strength of a cured product of the resultant redox-curing type composition may be lowered.

Preferably, at least a part of the polymerization accelerator (e) is dispersed in a powdery state in the composition. Dispersing the polymerization accelerator (e) in a powdery state makes it possible to secure a longer working time for the redox-curing type composition of the present invention. Moreover, in the case where the redox-curing type composition is applied to a wet body, such as a tooth structure, the polymerization accelerator is dissolved in the moisture present on the surface of the wet body, thereby increasing further the polymerization curabilities at the adhesion interface and inside the resin-impregnated layer. When the polymerization accelerator (e) is dispersed in a powdery state, the polymerization accelerator preferably has a water solubility of 1 mg/100 mL or more at ordinary temperature (25° C.). In the case where the solubility is less than 1 mg/100 mL, when the redox-curing type composition of the present invention is applied to the wet body, the polymerization accelerator (e) fails, at the adhesion interface, to be dissolved sufficiently in the moisture of the wet body. As a result, the effects to be exhibited when the polymerization accelerator (e) is dispersed in a powdery state are unlikely to be exhibited. Moreover, since the polymerization accelerator (e) tends to precipitate easily when having an excessively large particle diameter, the polymerization accelerator (e) preferably has an average particle diameter of 500 µm or less, more preferably 100 µm or less, and further preferably 50 µm or less. However, the average particle diameter preferably is 0.01 µm or more because an excessively small average particle diameter increases excessively the specific surface area of the powder, leading to possible deterioration in the handling property of the redox-curing type composition. That is, the polymerization accelerator (e) preferably has an average particle diameter of 0.01 to 500 μm, and more preferably 0.01 to 100 μm, when dispersed in a powdery state.

The shape of the polymerization accelerator (e) when dispersed in a powdery state is not particularly limited and may be any of various shapes such as a spherical shape, a needle shape, a plate shape and a crushed shape. The polymerization accelerator (e) in a powdery state may be prepared by any of known methods such as a grinding method and a freeze dry method.

In order to prepare the composition of the present invention as a dual cure type composition in which the polymerization is started also through irradiation with light, another known photopolymerization initiator may be added besides the redox polymerization initiator. Examples of the known photopolymerization initiator include α-diketones, ketals, thioxanthones, acylphosphine oxides, and α-aminoacetophenones.

Specific examples of the α-diketones include camphorquinone, benzyl, and 2,3-pentanedione.

Specific examples of the ketals include benzyl dimethylketal and benzyl diethylketal.

Specific examples of the thioxanthones include 2-chlorothioxanthone and 2,4-diethylthioxantone.

Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphine oxide, 2,4,6-trimethylbenzoylethoxyphenylphosphine oxide, and a water-soluble acylphosphine oxide compound disclosed in JP 3(1991)-57916 B.

Specific examples of the α-aminoacetophenones include 2-benzyl-2-dimethylamino-1-(4-morpholinophenyl)-butanone-1, 2-benzyl-2-diethylamino-1-(4-morpholinophenyl)-butanone-1, 2-benzyl-2-dimethylamino-1-(4-morpholinophenyl)-propanone-1, 2-benzyl-2-diethylamino-1-(4-morpholinophenyl)-propanone-1, 2-benzyl-2-dimethylamino-1-(4-morpholinophenyl)-pentanone-1, and 2-benzyl-2-diethylamino-1-(4-morpholinophenyl)-pentanone-1.

These photopolymerization initiators may be used independently or a plurality of them may be used in combination. The amount of the polymerization initiator to be added preferably is 0.01 to 10 parts by weight, and more preferably 0.5 to 5 parts by weight, with respect to 100 parts by weight of the total amount of the polymerizable monomer components included in the redox-curing type composition of the present invention.

Furthermore, in order to increase the photocuring property, the photopolymerization initiator may be used together with a polymerization promoter such as aldehydes and a thiol compound. Examples of the aldehydes include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde. Examples of the thiol compound include 3-mercaptopropyltrimethoxysilane, 2-mercaptobenzoxazole, decanethiol, and thiobenzoic acid. These polymerization promoters may be used independently or a plurality of them may be used in combination.

Furthermore, a filler may be added to the redox-curing type composition of the present invention in order to enhance the bond strength, handling property, flowability, X-ray opacity, and mechanical strength. The filler may be added independently or a plurality of it may be added in combination. Examples of the filler include an inorganic filler, an organic filler, and a complex filler of an inorganic filler and an organic filler.

Examples of the inorganic filler include: silica; a mineral, such as kaoline, clay, isinglass and mica, that contains silica as a base; and ceramics and glasses containing silica as a base and containing $Al_2O_3$, $B_2O_3$, $TiO_2$, $ZrO_2$, BaO, $La_2O_3$, SrO, ZnO, CaO, $P_2O_5$, $Li_2O$, $Na_2O$ or the like. As the glasses, lanthanum glass, barium glass, strontium glass, soda glass, lithium borosilicate glass, zinc glass, fluoroaluminosilicate glass, borosilicate glass, and bioglass are used suitably. Also, crystalline quartz, hydroxyapatite, alumina, titanium oxide, yttrium oxide, zirconia, calcium phosphate, barium sulphate, aluminium hydroxide, sodium fluoride, potassium fluoride, sodium monofluorophosphate, lithium fluoride, and ytterbium fluoride are used suitably. Specifically, fine particle silica having a primary particle diameter of 0.001 to 0.1 μm preferably are used from the viewpoint of bond strength and handling property. Examples of commercially-available products thereof include "Aerosil OX50", "Aerosil 50", "Aerosil 200", "Aerosil 380", "Aerosil R972" and "Aerosil 130" (trade names, all produced by Nippon Aerosil Co., Ltd.).

Examples of the organic filler include polymethyl methacrylate, polyethyl methacrylate, a polymer of multifunctional methacrylate, polyamide, polystyrene, polyvinyl chloride, chloroprene rubber, nitrile rubber, and styrene-butadiene rubber.

Examples of the complex filler of an inorganic filler and an organic filler include a complex filler obtained by dispersing an inorganic filler in an organic filler, and an inorganic/organic complex filler obtained by coating an inorganic filler with various polymers.

In order to enhance the curing property, mechanical strength and handling property, the fillers may be used after the surfaces thereof are treated beforehand with a known surface-treating agent such as a silane coupling agent. Examples of the surface-treating agent include vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, and γ-aminopropyltriethoxysilane.

The amount of the filler to be added preferably is 10 to 80% by weight, more preferably 30 to 80% by weight, and most preferably 50 to 75% by weight, based on the total weight of the composition of the present invention.

A fluorine ion-releasing material may be added to the redox-curing type composition of the present invention to provide a tooth structure with acid resistance. Examples of the fluorine ion-releasing material include a fluorine ion-releasing polymer such as a copolymer of methyl methacrylate and fluoride methacrylate, a fluorine ion-releasing material such as cetylamine hydrofluoride, and the fluoroaluminosilicate glass, sodium fluoride, potassium fluoride, sodium monofluorophosphate, lithium fluoride and ytterbium fluoride mentioned above as inorganic fillers.

An additive, such as a stabilizer (polymerization inhibitor), a colorant, a fluorescence agent and an ultraviolet absorber, may be added to the redox-curing type composition of the present invention. Moreover, an antibacterial material, such as cetylpyridinium chloride, benzalkonium chloride, (meth)acryloyloxydodecyl pyridinium bromide, (meth)acryloyloxyhexadecylpyridinium chloride, (meth)acryloyloxydecylammonium chloride and triclosan, may be added.

A known dye and pigment may be added to the composition of the present invention.

Even being free from water, the redox-curing type composition of the present invention including the above-mentioned components can exhibit a high bond strength by utilizing only the moisture contained in the wet body. Moreover, as described above, since water is a component that lowers the storage stability of the composition, the content of water in the redox-curing type composition of the present invention should be in a range that does not impair the storage stability. Preferably, the redox-curing type composition of the present invention is substantially free from water. The expression "to be substantially free from water" means that no water is added positively except for the water contained originally in each component of the composition. The content of water is, for example, 0.1% by weight or less based on the total weight of the composition of the present invention.

The redox-curing type composition of the present invention is suitable for medical applications and dental applications, and most suitable for dental applications. The redox-curing type composition of the present invention suitably can be used as an adhesive for biological hard tissues. Particularly, it is most suitable for dental cements.

If a product (an adhesive for biological hard tissues, particularly a dental cement) using the redox-curing type composition of the present invention is provided as a single part type product, the amine-based reducing agent (d) and the polymerization accelerator (e) react with the inorganic peroxide (c), decomposing the inorganic peroxide (c) during storage in some cases. In these cases, the amount of radicals to be generated decreases. Therefore, the product using the redox-curing type composition of the present invention preferably is a two part type product including a first part and a second part.

When the composition is dividedly packed into the first part and the second part, the first part contains the inorganic peroxide (c) and the second part contains the amine-based reducing agent (d) so that the inorganic peroxide (c) and the amine-based reducing agent (d) are contained in different parts, for example. The polymerizable monomer (a) having an acidic group, the polymerizable monomer (b) having no acidic group, and the polymerization accelerator (e) each may be contained in one or both of the first part and the second part. Preferably, the first part and the second part each contain the polymerizable monomer (a) and/or the polymerizable monomer (b) so that the first part and the second part become pasty. Here, from the viewpoint of storage stability, it is preferable that the polymerizable monomer (a) having an acidic group and the polymerization accelerator (e) are contained in different parts. Examples of preferable embodiment include: an embodiment in which the first part contains the inorganic peroxide (c), the polymerizable monomer (a) having an acidic group, and the polymerizable monomer (b) having no acidic group, whereas the second part contains the amine-based reducing agent (d), the polymerizable monomer (b) having no acidic group, and the polymerization accelerator (e); and an embodiment in which the first part contains the inorganic peroxide (c), the polymerizable monomer (b) having no acidic group and the polymerization accelerator (e), whereas the second part contains the amine-based reducing agent (d), the polymerizable monomer (a) having an acidic group, and the polymerizable monomer (b) having no acidic group.

The weight ratio at which the first part and the second part is mixed is preferably 1:10 to 5:1 from the viewpoint of the curing property and the time (working time) usable for an adhesion operation of the resultant composition.

When the product is a dental cement, a filler preferably is added to the first part and/or the second part from the viewpoint of the mechanical strength of the cured product.

An example of the method of using the two part type product will be described. The first part and the second part are mixed together to be a single part (the composition of the present invention) just before use, and then the composition is applied to a wet body. The curing reaction is accelerated at the adhesion interface because of the contact between the mixed composition and the moisture present on the surface of the wet body. With the completion of the curing reaction, the composition of the present invention bonds to the wet body. This will be described in detail by exemplifying an application to a tooth. In the case of filling the tooth cavity for restoration, the tooth cavity is cleaned by a common method, and then the composition of the present invention mixed into a single-part is filled into the tooth cavity. In the case of bonding a prosthesis material, such as a crown and an inlay, to an abutment tooth or a tooth cavity, an adhesion surface of the abutment tooth or the tooth cavity and an adhesion surface of the prosthesis material are cleaned, and then the composition of the present invention mixed into a single-part is applied to at least one of the adhesion surface of the abutment tooth or the tooth cavity and the adhesion surface of the prosthesis material to bond the composition thereto. Before the composition of the present invention is applied to the tooth surface, the tooth surface may be subjected to a known pretreatment such as etching with an acidic aqueous solution, modification with a primer, and simultaneous etching/modification with a primer capable of etching.

Use of the composition of the present invention in this manner makes it possible to achieve high storage stability as well as a higher bond strength to a wet body, particularly to a tooth structure (dentin) than those of conventional compositions. Therefore, the present invention can provide a composition that, even after being stored for a long time, maintains its curing time and curing property, suffers no decrease in bond strength, no change in color tone and no decrease in transparency, and has a high bond strength. Moreover, the composition of the present invention has high bond durability also to a crown restoration material such as metal and porcelain.

EXAMPLES

Hereinafter, the present invention will be described in further detail with reference to examples. The present invention is not limited to the examples described below. The following abbreviations are used hereinafter.

[Polymerizable Monomer (a) Having An Acidic Group]
MDP: 10-methacryloyloxydecyl dihydrogen phosphate
[Polymerizable Monomer (b) Having No Acidic Group]
Water-Soluble Polymerizable Monomer:
  HEMA: 2-hydroxyethylmethacrylate
Hydrophobic Polymerizable Monomer:
  Bis-GMA: 2,2-bis[4-(3-methacryloyloxy)-2-hydroxypropoxyphenyl]propane
  D-2.6E: 2,2-bis(methacryloyloxypolyethoxyphenyl)propane
  NPG: Neopentyl glycol dimethacrylate
[Inorganic Peroxide (c)]
  APS: Ammonium peroxodisulfate
  KPS: Potassium peroxodisulfate
  NaPS: Sodium peroxodisulfate
[Amine-Based Reducing Agent (d)]
  DEPT: N,N-bis(2-hydroxyethyl)-p-toluidine
  TTA: Triethanolamine
[Polymerization Accelerator (e)]
  TPBSS: Sodium 2,4,6-triisopropylbenzenesulfinate
  $Na_2SO_3$ Sodium sulfite The sodium sulfite used had been made finer as follows. An aqueous solution of sodium sulfite was prepared and frozen at −50° C., and then vacuum-dried in the frozen state. Thus, fine powder sodium sulfite was obtained.

[Others]

BPO: Benzoyl peroxide (organic peroxide)

[Filler]

Silane-treated quartz powder, silane-treated barium glass powder, and silane-treated colloidal silica powder were obtained in accordance with the following production methods.

Silane-Treated Quartz Powder:

Quartz (produced by MARUWA QUARTZ Co., Ltd.) was ground in a ball mill to obtain quartz powder having an average particle diameter of about 4.5 µm. 100 parts by weight of this quartz glass powder was subject to a surface treatment performed by a common method using 3 parts by weight of γ-methacryloyloxypropyltrimethoxysilane. Thus, silane-treated quartz powder was obtained.

Silane-Treated Barium Glass Powder:

Barium glass (produced by Esstech Inc., product code "Raysorb E-3000") was ground in a ball mill to obtain barium glass powder having an average particle diameter of about 2.4 µm. 100 parts by weight of this barium glass powder was subject to a surface treatment performed by a common method using 3 parts by weight of γ-methacryloyloxypropyltrimethoxysilane. Thus, silane-treated barium glass powder was obtained.

Silane-Treated Colloidal Silica Powder:

0.3 part by weight of acetic acid and 5 parts by weight of γ-methacryloyloxypropyltrimethoxysilane were added to 100 parts by weight of distilled water and then they were stirred. Further, 50 parts by weight of colloidal silica powder (produced by Japan Aerosil Inc., product name "Aerosil 130") was added thereto and then they were stirred for one hour. After water was removed by freeze drying, the mixture was heated at 80° C. for five hours. Thus, silane-treated colloidal silica powder was obtained.

Usually, peroxodisulfate commercially available as a reagent is crystalline powder having an average particle diameter of 0.5 to 1 mm. Each fine powder peroxodisulfate listed in Tables 1 to 3 can be obtained by the following methods.

Method 1

Prepare an aqueous solution of peroxodisulfate, freeze this aqueous solution at −50° C., and then vacuum-dry it in the frozen state.

Method 2

Prepare a saturated aqueous solution of peroxodisulfate, pour this solution into 0° C. ethanol, filter out the resultant crystal and wash the crystal with ethanol, and then air-dry the crystal.

Method 3

Prepare a saturated aqueous solution of peroxodisulfate, cool this aqueous solution rapidly to 0° C., and then filter out the resultant crystal and air-dry it.

Method 4

Mechanical Grinding and Sieving.

Among Methods 1 to 4, Method 1 was employed in the examples to obtain the fine powder. The average particle diameter of each peroxodisulfate fine powder was determined as a mean volume diameter after an image analysis was made on an electron microscope photograph of 100 particles or more using an image analysis software (Mac-View produced by Mountech Co., Ltd.)

Examples 1 to 14

In each example, the first part and the second part having respectively the compositions shown in Table 1 were prepared. The redox-curing type composition was dividedly packed into two parts so that the weight ratio between these two parts was 1:1. The first part was prepared by mixing the components other than the peroxodisulfate and filler, and then stirring the mixture to obtain a homogeneous solution, and thereafter mixing the solution with the peroxodisulfate that had been fine-powdered by the above-mentioned method and the filler, and deggasing the resultant. In the first part, the peroxodisulfate was dispersed in a powdery state. The second part was prepared by mixing the components other than the sodium 2,4,6-triisopropylbenzenesulfinate (hereinafter referred to as TPBSS), sodium sulfite and filler, then stirring the mixture to obtain a homogeneous solution, and thereafter mixing the solution with the TPBSS, sodium sulfite and filler, and deggasing the resultant. In the second part, the TPBSS and sodium sulfite were dispersed in a powdery state. Each of the dividedly-packed redox-curing type compositions was checked for curing time, tensile bond strength (Q1) to bovine dentine, discoloration when immersed in water at 50° C., and storage stability by the methods described below. Table 1 shows the results.

[Curing Time]

The first part and the second part were taken in the same amount and then mixed with each other, and the resultant mixture was filled into a micro tube. The mixture was taken out therefrom after a predetermined time elapsed from the start of the mixing, and sandwiched between slide glasses for microscope. The slide glasses were pressed against the mixture so as to apply a shearing force thereto, and the mixture was checked visually to see whether any inhomogeneous portion appeared therein. This checking was performed repeatedly while extending the time from the start of the mixing to the application of the shear force by 10 seconds each, until the curing was completed. The point of time at which an inhomogeneous portion appeared was defined as curing start time. The point of time at which the mixture stopped being deformed even under the pressing was defined as curing completion time.

[Tensile Bond Strength (Q1) to Bovine Dentine]

The labial surface of a bovine mandibular incisor was ground with silicon carbide paper under running water so as to expose a flat surface of dentin. The exposed flat surface was further ground with #1000 silicon carbide paper under running water. After the grinding, water on the surface was air-blown to be dried. An adhesive tape with a thickness of about 150 µm having a circular hole whose diameter was 3 mm was attached to the smooth surface that had been dried and thereby the adhesive area was defined. The first part and the second part of the dividedly-packed redox-curing type composition were mixed with each other at a weight ratio of 1:1 to prepare a cement composition. The cement composition was mounded on one end face (circular cross section) of a stainless steel cylindrical rod (with a diameter of 7 mm and a length of 2.5 cm). The end face with the cement composition mounded thereon was placed on the smooth surface (adherend) in the hole so that the center of the hole and the center of the stainless steel cylindrical rod substantially coincided with each other, and the stainless steel rod was pressed vertically against the smooth surface to be bonded thereto. A sample was thus prepared. Five samples were prepared in total. An excess portion of the cement composition forced out around the stainless steel cylindrical rod at the time of pressing was removed, and then each sample was allowed to stand still at room temperature for 30 minutes and immersed in distilled water. The sample that had been immersed in distilled water was allowed to stand still for 24 hours inside a thermostat whose temperature was maintained at 37° C. The sample was checked for tensile bond strength after it had been allowed to stand still at 37° C. for 24 hours. The tensile bond strength was measured with a universal testing machine (manufactured by Shimadzu Corporation) with the crosshead speed being set at 2 mm/min. Each of the tensile bond strengths obtained after the samples had been allowed to stand still at 37° C. for 24 hours shown in the table is an average of the values measured on the five test samples.

[Change in Color Tone when Immersed in Water at 50° C.]

The first part and the second part of the dividedly-packed redox-curing type composition were mixed with each other at a weight ratio of 1:1 to prepare a cement composition. This cement composition was sandwiched between two sheets of cover glasses to be formed into a disc shape with a thickness of 1 mm using a 1 mm gauge, and the resultant was allowed to stand still in a thermostat at 37° C. for one and a half hours. The cured product obtained was measured for color tone with a color difference meter, and the measured value was defined as an initial value. This cured product was immersed in distilled water at 50° C. and checked for color tone in three days. The difference between the value measured at this time and the initial value was defined as discoloration ($\Delta E^*$).

[Storage Stability]

The cement composition was stored in a thermostat at 50° C. for four weeks, and then taken out therefrom to be measured for curing time and tensile bond strength to bovine dentine by the above-mentioned methods.

Examples 15, and 17 to 20

A dental adhesive (A1) below was prepared. The aforementioned test of tensile bond strength (Q2) to bovine dentine was conducted by using this dental adhesive and the redox-curing type compositions of Examples 1, 2, 4, 11 and 12 to determine the bond strengths of the compositions when used in combination with the dental adhesive as a kit. Table 2 shows the results.

Dental Adhesive (A1):

| | |
|---|---|
| MDP | 10 parts by weight |
| HEMA | 45 parts by weight |
| Distilled water | 45 parts by weight |
| DEPT | 2 parts by weight |

[Tensile Bond Strength (Q2) to Bovine Dentine]

As in the above-mentioned test of the tensile bond strength (Q1) to bovine dentine, a bovine mandibular incisor was treated and an adhesive tape with a thickness of about 150 μm having a circular hole whose diameter was 3 mm was attached to the dentin serving as an adherend and thereby the adhesive area was defined. The dental adhesive was applied to the circular hole with a brush and was left for 10 seconds. Thereafter, the dental adhesive was dried using a dental air syringe until it lost fluidity. On the other hand, the first part and the second part of the dividedly-packed redox-curing type composition were mixed with each other at a weight ratio of 1:1 to prepare a cement composition. This cement composition was mounded on one end face (circular cross section) of a stainless steel cylindrical rod (with a diameter of 7 mm and a length of 2.5 cm). The end face with the cement composition mounded thereon was pressed against the smooth surface (adherend) in the hole so that the center of the hole, to which the dental adhesive had been applied, and the center of the stainless steel cylindrical rod substantially coincided with each other, and thereby the rod was bonded to the smooth surface. The resultant was left for 30 minutes to be cured and used as a sample. Five test samples were thus prepared. Subsequently, the thus obtained test pieces were immersed in distilled water and left for 24 hours in a thermostat set at 37° C. Then, the test pieces were taken out therefrom to be measured for tensile bond strength. The tensile bond strength was measured with a universal testing machine (manufactured by Shimadzu Corporation) with a crosshead speed being set at 2 mm/min. An average of the values measured on the five samples was defined as the tensile bond strength of the samples.

Example 16

A dental adhesive (A2) below was prepared. The test of tensile bond strength (Q2) to bovine dentine was conducted using this dental adhesive and the redox-curing type composition of Example 1 to determine the bond strength of the composition when used in combination with the dental adhesive as a kit. Table 2 shows the result.

Dental Adhesive (A2):

| | |
|---|---|
| MDP | 10 parts by weight |
| HEMA | 45 parts by weight |
| Bis-GMA | 35 parts by weight |
| Distilled water | 15 parts by weight |
| DEPT | 2 parts by weight |
| Ethanol | 10 parts by weight |

Comparative Example 1

A redox-curing type composition (comparative composition) dividedly packed, at a weight ratio of 1:1, into the first part and the second part having respectively the compositions shown in Table 3 was produced as in Examples 1 to 14, except that benzoyl peroxide (BPO) was used instead of peroxodisulfate in preparing the first part. The dividedly-packed redox-curing type composition was checked for curing time, tensile bond strength to a tooth structure (bovine dentine), discoloration when immersed in water at 50° C., and storage stability by the above-mentioned methods. Table 3 shows the results.

Comparative Examples 2 to 5

Redox-curing type compositions (comparative compositions) dividedly packed, at a weight ratio of 1:1, into the first part and the second part having respectively the compositions shown in Table 3 were produced as in Examples 1 to 14, except that the aromatic amine (d-1) and the aliphatic amine (d-2) were used at a content ratio (weight ratio) other than (d-1):(d-2) of 5:1 to 1:50 in preparing the second part. Each of the dividedly-packed redox-curing type compositions was checked for curing time, tensile bond strength to a tooth structure (bovine dentine), discoloration when immersed in water at 50° C., and storage stability by the above-mentioned methods. Table 3 shows the results.

TABLE 1

|  |  |  | Composition list (unit: part by weight) | | | | | | |
|---|---|---|---|---|---|---|---|---|---|
|  |  |  | Example 1 | Example 2 | Example 3 | Example 4 | Example 5 | Example 6 | Example 7 |
| First part | MDP |  | 20 | 20 | 20 | 20 | 20 | 20 | 20 |
|  | Bis-GMA |  | 40 | 40 | 40 | 40 | 40 | 40 | 40 |
|  | HEMA |  | 40 | 40 | 40 | 40 | 40 | 40 | 40 |
|  | Peroxodi-sulfate | APS | — | — | — | — | — | — | 2 |
|  |  | KPS | 2 | 2 | 2 | 0.5 | 0.5 | 1 | — |
|  |  | NaPS | — | — | — | — | — | — | — |
|  |  | Average particle diameter (μm) | 1.0 | 1.0 | 25.2 | 1.0 | 1.0 | 1.0 | 4.6 |
|  | Photopolymerization initiator |  | 0.15 | 0.15 | 0.15 | 0.15 | 0.15 | 0.15 | 0.15 |
|  | Silane-treated quartz powder |  | 288 | 288 | 288 | 288 | 288 | 288 | 288 |
|  | Silane-treated colloidal silica powder |  | 12 | 12 | 12 | 12 | 12 | 12 | 12 |
| Second part | D-2.6E |  | 72 | 72 | 72 | 72 | 72 | 72 | 72 |
|  | NPG |  | 25 | 25 | 25 | 25 | 25 | 25 | 25 |
|  | Bis-GMA |  | 3 | 3 | 3 | 3 | 3 | 3 | 3 |
|  | DEPT |  | 1 | 0.5 | 1 | 0.25 | 0.1 | 0.25 | 1 |
|  | TTA |  | 2 | 2.5 | 2 | 2.75 | 2.9 | 2.75 | 2 |
|  | TPBSS |  | 2 | 2 | 2 | 2 | 1 | 2 | 2 |
|  | Sodium sulfite |  | — | — | — | 1 | 1 | 1 | — |
|  | Silane-treated barium glass powder |  | 288 | 288 | 288 | 288 | 288 | 288 | 288 |
|  | Silane-treated colloidal silica powder |  | 12 | 12 | 12 | 12 | 12 | 12 | 12 |
|  | DEPT(d-1):TTA(d-2) |  | 1:2 | 1:5 | 1:2 | 1:11 | 1:29 | 1:11 | 1:2 |
| Dental adhesive |  |  | — | — | — | — | — | — | — |
| Curing time | Start (minute) |  | 3.5 | 4.5 | 4.5 | 5.5 | 7.0 | 5.0 | 2.5 |
|  | Completion (minute) |  | 4.5 | 5.0 | 6.0 | 7.5 | 9.5 | 6.5 | 3.0 |
| Tensile bond strength to dentine (MPa) |  |  | 12.2 | 11.5 | 10.1 | 12.9 | 10.2 | 13.1 | 12.3 |
| ΔE*, change in color tone after storage in water at 50° C. for 3 days. |  |  | 4.0 | 2.6 | 3.5 | 1.2 | 0.8 | 2.0 | 3.9 |
| Storage stability | Curing time | Start (minute) | 3.5 | 4.5 | 5.0 | 5.5 | 7.5 | 5.0 | 3.0 |
|  |  | Completion (minute) | 4.5 | 5.5 | 5.5 | 7.5 | 9.5 | 6.0 | 3.5 |
|  | Tensile bond strength to dentine (MPa) |  | 12.8 | 10.9 | 10.0 | 12.0 | 9.7 | 12.8 | 12.5 |

|  |  |  | Composition list (unit: part by weight) | | | | | | |
|---|---|---|---|---|---|---|---|---|---|
|  |  |  | Example 8 | Example 9 | Example 10 | Example 11 | Example 12 | Example 13 | Example 14 |
| First part | MDP |  | 20 | 20 | 20 | 20 | 20 | 20 | 20 |
|  | Bis-GMA |  | 40 | 40 | 40 | 40 | 40 | 40 | 40 |
|  | HEMA |  | 40 | 40 | 40 | 40 | 40 | 40 | 40 |
|  | Peroxodi-sulfate | APS | 2 | 2 | — | — | — | — | — |
|  |  | KPS | — | — | — | 2 | 2 | 2 | 2 |
|  |  | NaPS | — | — | 2 | — | — | — | — |
|  |  | Average particle diameter (μm) | 4.6 | 4.6 | 9.3 | 1.0 | 1.0 | 1.0 | 1.0 |
|  | Photopolymerization initiator |  | 0.15 | 0.15 | 0.15 | 0.15 | 0.15 | 0.15 | 0.15 |
|  | Silane-treated quartz powder |  | 288 | 288 | 288 | 288 | 288 | 288 | 288 |
|  | Silane-treated colloidal silica powder |  | 12 | 12 | 12 | 12 | 12 | 12 | 12 |
| Second part | D-2.6E |  | 72 | 72 | 72 | 72 | 72 | 72 | 72 |
|  | NPG |  | 25 | 25 | 25 | 25 | 25 | 25 | 25 |
|  | Bis-GMA |  | 3 | 3 | 3 | 3 | 3 | 3 | 3 |
|  | DEPT |  | 0.5 | 0.25 | 1 | 2.4 | 2 | 0.12 | 0.07 |
|  | TTA |  | 2.5 | 2.75 | 2 | 0.6 | 1 | 2.88 | 2.93 |
|  | TPBSS |  | 2 | 2 | 2 | 2 | 2 | 2 | 2 |
|  | Sodium sulfite |  | — | — | — | — | — | — | — |
|  | Silane-treated barium glass powder |  | 288 | 288 | 288 | 288 | 288 | 288 | 288 |
|  | Silane-treated colloidal silica powder |  | 12 | 12 | 12 | 12 | 12 | 12 | 12 |
|  | DEPT(d-1):TTA(d-2) |  | 1:5 | 1:11 | 1:2 | 4:1 | 2:1 | 1:25 | 1:40 |
| Dental adhesive |  |  | — | — | — | — | — | — | — |
| Curing time | Start (minute) |  | 3.5 | 5.0 | 5.5 | 4.0 | 2.8 | 6.3 | 10.8 |
|  | Completion (minute) |  | 4.0 | 6.0 | 6.5 | 5.5 | 3.9 | 8.0 | 13.5 |
| Tensile bond strength to dentine (MPa) |  |  | 10.3 | 8.4 | 9.4 | 8.5 | 11.0 | 6.3 | 5.6 |
| ΔE*, change in color tone after storage in water at 50° C. for 3 days. |  |  | 2.4 | 1.2 | 4.6 | 7.0 | 5.5 | 2.9 | 4.3 |
| Storage stability | Curing time | Start (minute) | 3.5 | 5.5 | 5.5 | 5.0 | 2.9 | 6.5 | 11.0 |
|  |  | Completion (minute) | 4.5 | 6.0 | 6.0 | 6.5 | 4.1 | 8.8 | 14.5 |
|  | Tensile bond strength to dentine (MPa) |  | 9.9 | 8.1 | 9.0 | 7.2 | 10.5 | 5.9 | 5.0 |

TABLE 2

Composition list (unit: part by weight)

| | | Example 15 | Example 16 | Example 17 | Example 18 | Example 19 | Example 20 |
|---|---|---|---|---|---|---|---|
| First part | MDP | 20 | 20 | 20 | 20 | 20 | 20 |
| | Bis-GMA | 40 | 40 | 40 | 40 | 40 | 40 |
| | HEMA | 40 | 40 | 40 | 40 | 40 | 40 |
| | Peroxodisulfate APS | — | — | — | — | — | — |
| | KPS | 2 | 2 | 2 | 0.5 | 2 | 2 |
| | NaPS | — | — | — | — | — | — |
| | Average particle diameter (μm) | 1.0 | 1.0 | 1.0 | 1.0 | 1.0 | 1.0 |
| | Photopolymerization initiator | 0.15 | 0.15 | 0.15 | 0.15 | 0.15 | 0.15 |
| | Silane-treated quartz powder | 288 | 288 | 288 | 288 | 288 | 288 |
| | Silane-treated colloidal silica powder | 12 | 12 | 12 | 12 | 12 | 12 |
| Second part | D-2.6E | 72 | 72 | 72 | 72 | 72 | 72 |
| | NPG | 25 | 25 | 25 | 25 | 25 | 25 |
| | Bis-GMA | 3 | 3 | 3 | 3 | 3 | 3 |
| | DEPT | 1 | 1 | 0.5 | 0.25 | 2.4 | 2 |
| | TTA | 2 | 2 | 2.5 | 2.75 | 0.6 | 1 |
| | TPBSS | 2 | 2 | 2 | 2 | 2 | 2 |
| | Sodium sulfite | — | — | — | 1 | — | — |
| | Silane-treated barium glass powder | 288 | 288 | 288 | 288 | 288 | 288 |
| | Silane-treated colloidal silica powder | 12 | 12 | 12 | 12 | 12 | 12 |
| | DEPT(d-1):TTA(d-2) | 1:2 | 1:2 | 1:5 | 1:11 | 4:1 | 2:1 |
| Dental adhesive | | A-1 | A-2 | A-1 | A-1 | A-1 | A-1 |
| Curing time | Start (minute) | — | — | — | — | — | — |
| | Completion (minute) | — | — | — | — | — | — |
| Tensile bond strength to dentine (MPa) | | 18.6 | 17.8 | 15.0 | 18.8 | 14.4 | 15.1 |
| ΔE*, change in color tone after storage in water at 50° C. for 3 days. | | — | — | — | — | — | — |
| Storage stability | Curing time Start (minute) | — | — | — | — | — | — |
| | Completion (minute) | — | — | — | — | — | — |
| | Tensile bond strength to dentine (MPa) | — | — | — | — | — | — |

TABLE 3

Composition list (unit: part by weight)

| | | C. Example 1 | C. Example 2 | C. Example 3 | C. Example 4 | C. Example 5 |
|---|---|---|---|---|---|---|
| First part | MDP | 20 | 20 | 20 | 20 | 20 |
| | Bis-GMA | 40 | 40 | 40 | 40 | 40 |
| | HEMA | 40 | 40 | 40 | 40 | 40 |
| | Peroxodisulfate APS | — | — | — | — | — |
| | KPS | — | 2 | 2 | 2 | 2 |
| | NaPS | — | — | — | — | — |
| | Average particle diameter (μm) | — | 1.0 | 1.0 | 1.0 | 1.0 |
| | BPO | 3 | — | — | — | — |
| | Photopolymerization initiator | 0.15 | 0.15 | 0.15 | 0.15 | 0.15 |
| | Silane-treated quartz powder | 288 | 288 | 288 | 288 | 288 |
| | Silane-treated colloidal silica powder | 12 | 12 | 12 | 12 | 12 |
| Second part | D-2.6E | 72 | 72 | 72 | 72 | 72 |
| | NPG | 25 | 25 | 25 | 25 | 25 |
| | Bis-GMA | 3 | 3 | 3 | 3 | 3 |
| | DEPT | 1 | 2.85 | 0.05 | 3 | — |
| | TTA | 2 | 0.15 | 2.95 | — | 3 |
| | TPBSS | 2 | 2 | 2 | 2 | 2 |
| | Silane-treated barium glass powder | 288 | 288 | 288 | 288 | 288 |
| | Silane-treated colloidal silica powder | 12 | 12 | 12 | 12 | 12 |
| | DEPT(d1):TTA(d2) | 1:2 | 19:1 | 1:59 | 3:0 | 0:3 |
| Curing time | Start (minute) | 4.0 | 4.5 | 20 or more | 4.5 | 20 or more |
| | Completion (minute) | 5.0 | 5.5 | 20 or more | 6.0 | 20 or more |
| Tensile bond strength to dentine (MPa) | | 5.4 | 7.8 | 2.8 | 6.7 | 2.5 |
| ΔE*, change in color tone after storage in water at 50° C. for 3 days. | | 4.4 | 13.1 | 4.5 | 13.5 | 4.1 |
| Storage stability | Curing time Start (minute) | 8.5 | 9.0 | 20 or more | 10.0 | 20 or more |
| | Completion (minute) | 11.0 | 11.5 | 20 or more | 14.0 | 20 or more |
| | Tensile bond strength to dentine (MPa) | 3.0 | 4.1 | 2.9 | 3.4 | 2.1 |

As shown in Table 1, the redox-curing type compositions of the present invention used in Examples 1 to 14 each exhibited a high bond strength to bovine dentine. In contrast, as shown in Table 3, the redox-curing type composition used in Comparative Example 1 achieved a low bond strength to bovine dentine. Presumably, the reason is as follows. In the redox-curing type composition of Comparative Example 1, the organic peroxide was in a dissolved state, and thus the effect that the organic peroxide was dissolved at the adhesion interface and highly concentrated thereat was not obtained.

Moreover, since the penetration effect of the organic peroxide into the resin-impregnated layer formed on the dentin was low, the polymerization curing property in the resin-impregnated layer was low.

As shown in Table 1, the redox-curing type compositions of the present invention used in Examples 1 to 14 each exhibited a curing time and a bond strength to the bovine dentine comparable to those they had before being stored even after being stored in the thermostat at 50° C. for four weeks. Presumably, this is because the inorganic peroxide (c) was in an insoluble solid state in the composition and the decomposition of the inorganic peroxide (c) hardly proceeded. In contrast, as shown in Table 3, the redox-curing type composition used in Comparative Example 1 exhibited a longer curing time and a lower bond strength to bovine than those it had before being stored, after being stored in the thermostat at 50° C. for four weeks. Presumably, this is because in the redox-curing type composition of Comparative Example 1, the organic peroxide, which is thermally unstable, was in a dissolved state in the composition, and thus the decomposition of the organic peroxide was accelerated during the time when the composition was stored at 50° C. and its absolute quantity was reduced.

As shown in Table 1, the cured products produced from the redox-curing type compositions of the present invention used in Examples 1 to 14 each had a relatively small value of $\Delta E^*$, which indicates a difference between the value of color tone they had after being immersed in water at 50° C. for three days and the initial value. In contrast, as shown in Table 3, the cured products produced from the redox-curing type compositions used in Comparative Examples 2 and 4 each had a larger value of $\Delta E^*$, which indicates a difference between the value of color tone they had after being immersed in water at 50° C. for three days and the initial value, than those of Examples 1 to 14. Presumably, this is because the content ratio (weight ratio) between the aromatic amine and the aliphatic amine was not appropriate and the ratio of the aromatic amine was higher than it should be. Moreover, in Comparative Examples 2 and 4, the compositions stored in the thermostat at 50° C. for four weeks each had a significantly longer curing time and lower bond strength to bovine dentine than those they had immediately after being prepared. Presumably, this is because the content ratio (weight ratio) between the aromatic amine and the aliphatic amine was not appropriate. Moreover, in Comparative Examples 3 and 5, the curing time was significantly longer and the bond strength to bovine dentine was lower than those in Examples 1 to 14. Presumably, this is because the content ratio (weight ratio) between the aromatic amine and the aliphatic amine was not appropriate and the redox reactivity was lowered accordingly, resulting in lower polymerization curing property.

As shown in Table 2, the redox-curing type compositions of the present invention used in Examples 15 to 20 each exhibited a high bond strength to bovine dentine even when used in combination with the dental adhesive as a kit.

INDUSTRIAL APPLICABILITY

The present invention can be used suitably for, for example, restoration of wet bodies, such as biological hard tissues like teeth and bones, that contain moisture.

The invention claimed is:

1. A redox-curing type composition comprising a polymerizable monomer (a) having an acidic group, a polymerizable monomer (b) having no acidic group, a powdery inorganic peroxide (c) with an average particle diameter of 0.01 to 50 μm, an amine-based reducing agent (d), and a polymerization accelerator (e),
    wherein the amine-based reducing agent (d) comprises an aromatic amine (d–1) and an aliphatic amine (d–2), and a weight ratio (d–1):(d–2) therebetween is 5:1 to 1:50.

2. The redox-curing type composition according to claim 1, wherein the composition is substantially free from water.

3. The redox-curing type composition according to claim 1, wherein the polymerization accelerator (e) is at least one selected from the group consisting of sodium benzenesulfinate, sodium p-toluenesulfinate, sodium 2,4,6-triisopropylbenzenesulfinate, sodium sulfite, potassium sulfite, calcium sulfite, ammonium sulfite, sodium bisulfate, and potassium bisulfate.

4. The redox-curing type composition according to claim 1, wherein at least a part of the polymerization accelerator (e) is contained in a powdery state.

5. The redox-curing type composition according to claim 1, wherein the inorganic peroxide (c) is a peroxodisulfate.

6. The redox-curing type composition according to claim 1, wherein the inorganic peroxide (c) is obtained by a freeze dry method.

7. A dental cement comprising:
    a first part containing a powdery inorganic peroxide (c) with an average particle diameter of 0.01 to 50 μm; and
    a second part containing an amine-based reducing agent (d),
    wherein the amine-based reducing agent (d) comprises an aromatic amine (d–1) and an aliphatic amine (d–2), and a weight ratio (d–1):(d–2) therebetween is 5:1 to 1:50, and
    wherein a polymerizable monomer (a) having an acidic group, a polymerizable monomer (b) having no acidic group, and a polymerization accelerator (e) each are contained in one or both of the first part and the second part.

* * * * *